(12) United States Patent
Payne et al.

(10) Patent No.: US 11,821,417 B2
(45) Date of Patent: *Nov. 21, 2023

(54) FLUID HANDLING ASSEMBLY AND RELATED TUBE SET AND METHOD FOR USE IN SURGICAL PROCEDURES

(71) Applicant: MISONIX, LLC, Farmingdale, NY (US)

(72) Inventors: Timothy John Payne, Santa Ana, CA (US); Scott LaVoy Conway, Yorba Linda, CA (US); Robert Paul Mayercheck, Irvine, CA (US)

(73) Assignee: MISONIX, INCORPORATED, Farmingdale, NY (US)

( * ) Notice: Subject to any disclaimer, the term of this patent is extended or adjusted under 35 U.S.C. 154(b) by 274 days.

This patent is subject to a terminal disclaimer.

(21) Appl. No.: 17/235,308

(22) Filed: Apr. 20, 2021

(65) Prior Publication Data

US 2021/0299345 A1    Sep. 30, 2021

Related U.S. Application Data

(63) Continuation of application No. 16/169,569, filed on Oct. 24, 2018, now Pat. No. 11,007,308.

(51) Int. Cl.
*A61M 5/142* (2006.01)
*F04B 43/12* (2006.01)
*A61M 1/00* (2006.01)
*A61M 3/02* (2006.01)
(Continued)

(52) U.S. Cl.
CPC ........... *F04B 43/1292* (2013.01); *A61M 1/77* (2021.05); *A61M 1/80* (2021.05); *A61M 3/0258* (2013.01); *A61B 1/125* (2013.01); *A61B 2018/00011* (2013.01); *A61M 2205/3331* (2013.01)

(58) Field of Classification Search
CPC .............. A61M 1/0058; A61M 1/0062; A61M 5/14232; A61M 2205/12; A61M 2205/6045; A61M 2205/6054; A61M 2205/6065
See application file for complete search history.

(56) References Cited

U.S. PATENT DOCUMENTS

| | | | |
|---|---|---|---|
| 4,155,362 A | 5/1979 | Jess | F04B 43/1284 604/507 |
| 5,213,483 A * | 5/1993 | Flaherty | F04B 43/0072 417/474 |
| 5,403,277 A | 4/1995 | Dodge et al. | |

(Continued)

FOREIGN PATENT DOCUMENTS

WO    WO 2017/083733 A1    5/2017

*Primary Examiner* — Laura A Bouchelle
(74) *Attorney, Agent, or Firm* — R. Neil Sudol; Henry D. Coleman

(57) ABSTRACT

A fluid handling system for a surgical procedure includes a console and a tubing set. The console exhibits a peristaltic pump, a pinch valve, one above the other. Two recessed seats are located to the left and right sides of the pump and valve. The tubing set includes an irrigation tube and an aspiration tube each coupled to a pair of magnetic disks disposable in respective ones of the recessed seats. Upon such disposition, the irrigation tube is disposable in operative engagement with the peristaltic pump and the aspiration tube is insertable into a slot of the pinch valve.

16 Claims, 3 Drawing Sheets

(51) Int. Cl.
*A61B 1/12* (2006.01)
*A61B 18/00* (2006.01)

(56) References Cited

U.S. PATENT DOCUMENTS

| | | | |
|---|---|---|---|
| 5,460,490 | A | 10/1995 | Carr et al. |
| 6,319,223 | B1 | 11/2001 | Wortrich et al. |
| 7,273,359 | B2 | 9/2007 | Blight ................ F04B 43/1253 417/477.13 |
| 7,556,481 | B2 | 7/2009 | Moubayed .............. F04B 43/12 417/477.1 |
| 7,883,489 | B2 * | 2/2011 | Guignard .............. A61M 3/022 604/35 |
| 9,200,628 | B2 | 12/2015 | Zupp .................. A61M 5/14232 |
| 11,007,308 | B2 * | 5/2021 | Payne ..................... A61M 1/80 |
| 2008/0154095 | A1 | 6/2008 | Stubkjaer et al. |
| 2008/0214994 | A1 | 9/2008 | Guignard ............ A61M 3/0258 604/65 |
| 2009/0043252 | A1 | 2/2009 | Haylor ................ H05K 5/0234 604/67 |
| 2011/0300010 | A1 | 12/2011 | Jarnagin |
| 2012/0065482 | A1 | 3/2012 | Robinson et al. |
| 2013/0131585 | A1 | 5/2013 | Eubanks et al. |
| 2016/0287779 | A1 | 10/2016 | Orczy-Timko et al. |

\* cited by examiner

FLUID HANDLING ASSEMBLY AND RELATED TUBE SET AND METHOD FOR USE IN SURGICAL PROCEDURES

CROSS-REFERENCE TO RELATED APPLICATION

This application is a continuation of application Ser. No. 16/169,569 filed Oct. 24, 2018, now U.S. Pat. No. 11,007,308.

BACKGROUND OF THE INVENTION

The present invention relates to moving fluids in surgical procedures. More particularly, this invention relates to a fluid handling assembly including a console and a disposable tubing set. This invention also relates to the tubing set for use with the console. The invention also pertains to a method including the disposition of tubing in association with a pump and a pinch valve. The method is of particular use in ultrasonic surgical procedures, for irrigating and removing debris from a surgical site.

In ultrasonic surgical procedures, the head of an ultrasonically vibrating probe is placed into pressure-wave transmitting contact with tissue of a patient. The probe may be an ablating device, a debriding instrument, or a suction instrument, among others. Using an ultrasonic probe requires the delivery of an irrigant to the instrument and to the tissue in order to prevent temperature elevation to a degree that would cause necrosis. The cooling liquid must naturally be removed from the site into order to make way for further coolant. The removal entails suction that also removes entrained tissue particles.

Surgical equipment includes irrigation tubing and suction tubing as well as a pump mechanism for moving the irrigant to the surgical site, for instance, via the ultrasonic probe or a sheath surrounding the probe, and an aspiration or vacuum source connected to the suction tubing. A technician generally sets up the fluid handling circuits prior to the surgical procedure. On occasion, there are errors such as mixing the irrigation tubing and the suction tubing, which prevents proper operation of the assembly.

SUMMARY OF THE INVENTION

The present invention aims to provide a tubing set and associated console that facilitate the preparation of a fluids handling system prior to surgery.

The present invention further aims to provide such a tubing set and associated console that significantly reduce, if not eliminate, errors in setting up a surgical fluids handling assembly.

The present invention also contemplates an associated method of setting up a fluids handling assembly or system.

A fluid handling system for a surgical treatment comprises, in accordance with the present invention, a console and a tubing set.

The console includes a housing having a panel, a peristaltic pump, a pinch valve, and a first seat and a second seat on the housing panel. The peristaltic pump is mounted to the housing and extends outwardly from the panel. More specifically, the pump includes a roller set and an anvil that are movably attached to a pump casing, the roller set being rotatable about an axis perpendicular to the housing panel and the anvil being movable from a neutral position to a closed position for clamping a tube between the roller set and a curved inside surface of the anvil. The pinch valve is mounted to the housing panel and has a slot or gap between two jaws movable relative to one another to selectively restrict flow through a tube inserted into the slot. The peristaltic pump and the pinch valve are spaced from one another along a line. The seats are disposed on the housing panel on opposite sides of the line.

The tubing set, which is intended to be disposable rather than reusable, includes an irrigation tube, an aspiration tube, a first attachment element, and a second attachment element. The irrigation tube and the aspiration tube are each coupled to both the first attachment element and the second attachment element. The first attachment element is seatable in the first seat on the console housing panel while the second attachment element is seatable in the second seat. The irrigation tube and the aspiration tube are coupled to the first attachment element and the second attachment element so that the irrigation tube and the aspiration tube extend in spaced relation to one another between the first attachment element and the second attachment element, at least when the attachment elements are spaced from one another by a distance approximately equal to the distance between the first seat and the second seat on the console panel. The irrigation tube is positionable in operative engagement with the roller set and the anvil while the aspiration tube is insertable into the slot of the pinch valve upon seating of the first attachment element in the first seat and seating of the second attachment element in the second seat.

The console preferably further comprises first coupling elements at the first seat and the second seat, while the first attachment element and the second attachment element include second coupling elements that cooperate with respective ones of the first coupling elements to releasably fasten the first attachment element and the second attachment element to the housing panel at the first seat and the second seat, respectively.

The coupling elements may include magnets. Other, alternative, coupling elements may take the form of snap-lock fasteners, adhesive layers, hook-and-loop fasteners, etc.

Pursuant to another feature of the present invention, the seats are recesses of different geometries in the console housing panel. The first attachment element and the second attachment element have geometries corresponding to the geometries of respective ones of the recesses. Thus at least one of the attachment elements, said the second element, is disposable only in the second seat and cannot be seated in the first seat owing to a mismatch in size or shape.

Pursuant to additional features of the present invention, the first attachment element and the second attachment element are disks of different sizes, the first seat and the second seat having different sizes congruent with respective ones of the disks. The disks may be provided on one side (an outer side) with finger grips for facilitate manipulation of the tubing set during assembly of the fluid handling system.

The console may further include a plurality of indicators such as LED lights that signal successful seating of the first attachment element and the second attachment element in the first seat and the second seat, respectively, and successful placement of the irrigation tube between the roller set and the anvil of the peristaltic pump.

The console may also include an air bubble detector at the second seat. The air bubble detector is so located to be juxtaposed to the irrigation tube upon seating of the second attachment element in the second seat. More particularly, the air bubble detector may be housed in a projection on the second seat that is inserted into a hole in the rear or inner side of the second attachment element. The irrigation tube extends across the hole so as to automatically insert into a slot in the projection upon the seating of the second attachment element in the second seat on the housing panel of the console. The air bubble detector may take the form of an ultrasound sensor.

The panel is preferably a side panel of the housing, and the peristaltic pump and the pinch valve are preferably located vertically one above the other.

The present invention is directed in part to a fluid handling tubing set for use in surgical interventions. The tubing set, described above, is utilizable with a console as described above.

Concomitantly, the present invention contemplates a console as described above.

A surgical method in accordance with the present invention comprises providing a tubing set for carrying fluids, the tubing set including a first tube, a second tube, a first attachment element, and a second attachment element, the first tube and the second tube each being coupled to both the first attachment element and the second attachment element. The first attachment element and the second attachment element have different geometries. The method includes seating the first attachment element in a first seat on a panel of a console and seating the second attachment element in a second seat on the panel of the console so that the first tube and the second tube extend in spaced relation to one another between the first attachment element and the second attachment element. Thereafter, the first tube is manipulated so as to dispose a portion of the first tube in operative engagement with a roller set and an anvil of the console projecting from the panel, and the second tube is manipulated so as to insert the second tube into a slot or gap of a pinch valve of the console projecting from the panel.

DETAILED DESCRIPTION

A fluid handling system 10 for use in a surgical treatment procedure includes a console 12 and a tubing set 14.

Figure 1:
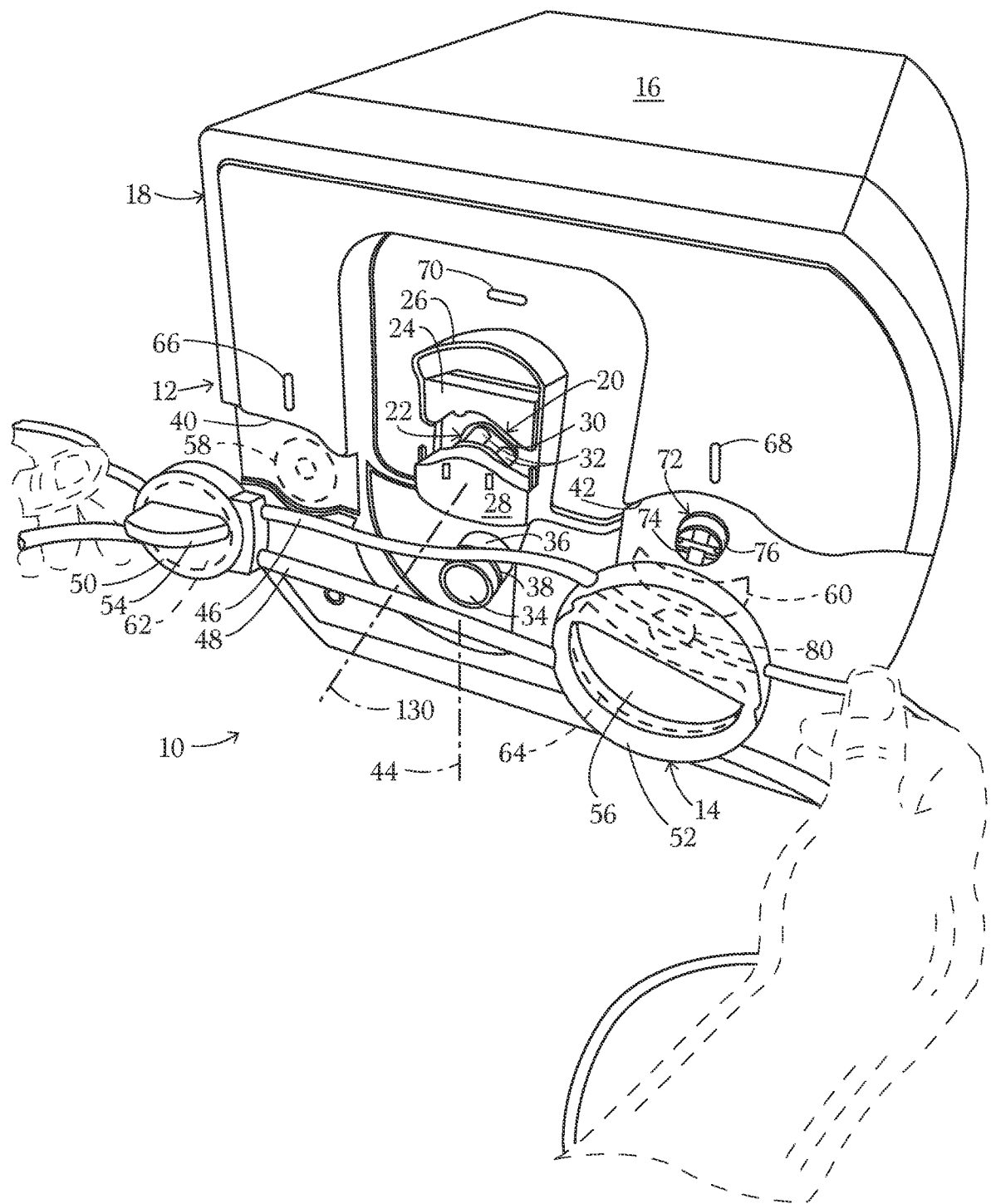
FIG. 1 is a perspective view of a fluid handling system particularly including a tubing set and a console, showing the tubing set spaced from an d in position for attachment to the console, in accordance with the present invention.

Console 12 includes a housing 16 with a side panel 18. A peristaltic pump 20 is mounted to housing 16 on side panel 18 and includes a roller set 22 and an anvil 24, as well as a cover 26. Roller set 22 is held at an outer end by a bracket 28 for rotation about an axis 30 oriented perpendicular to panel 18. Cover 26 is hingedly mounted to a pump casing (not separately designated) and, when rotated downwardly from a neutral position shown in FIG. 1 to a closed position shown in FIG. 3, moves anvil 24 toward roller set 22, so that a curved surface or face 30 of the anvil is placed adjacent to rollers 32 of roller set 22.

Console 12 further includes a solenoid-operated pinch valve 34 that comprises two relatively movable jaws (not separately designated) disposed inside a sleeve 36 mounted to panel 18 and formed with a transverse slot 38. Pinch valve 34 is spaced from peristaltic pump 20, including roller set 22 and anvil 24, in a plane or direction parallel to panel 18.

Console 12 further includes, molded into side panel 18, a first seat 40 and a second seat 42 in the form of circular or oval recesses of different geometries. More specifically, seats 40 and 42 may be of different shapes and/or different sizes. In the embodiment illustrated in the drawings, seat 42 is larger than seat 40.

Peristaltic pump 20 and solenoid pinch valve 34 are disposed one above the other and thereby define a vertical line or plane 44. Seats 40 and 42 are disposed on side panel 18 on opposite sides of line or plane 44.

Tubing set 14 includes an irrigation tube 46, an aspiration tube 48, a first attachment disk 50, and a second attachment disk 52. Irrigation tube 46 and aspiration tube 48 are each coupled to both first attachment disk 50 and second attachment disk 52. Disks 50 and 52 may be formed by bonding two half disks to one another, sandwiching tubes 46 and 48 between the half disks in each case. Disks 50 and 52 are each provided on major outer side or face (not designated) with a respective finger grip 54 and 56 in the form of a ring or flange projecting orthogonally to the respective major outer side or face for facilitating manipulation of the disks during an assembly procedure.

Typically, a technician grasping finger grips 54 and 56 will place disks 50 and 52 in recesses or seats 40 and 42 with major outer sides or faces of the disks in the seats so that the disks extend in parallel relation to each other and panel 18. Attachment is of a quick-release type owing to magnets 58 and 60 (or magnets and metal elements) positioned in housing 16 adjacent seats 40 and 42 and magnetic counterparts 62 and 64 attached to disks 50 and 52. Alternative coupling elements such as snap-lock fasteners, adhesive layers, hook-and-loop fasteners, etc., may be used instead of magnets.

Disks 50 and 52 have different geometries, that is, different sizes and/or shapes, that are respectively congruent with the geometries of seats 40 and 42 so that disks 50 and 52 are seatable only in seats 40 and 42, respectively. This ensures that irrigation tube 46 is located above aspiration tube 48 once attachment disks 50 and 52 are seated on panel 18. Irrigation tube 46 and aspiration tube 48 are coupled to attachment disks 50 and 52 so that tubes 46 and 48 extend in spaced relation to one another between the disks and in a plane parallel to panel 18, when the disks are placed into seats 40 and 42.

Figure 2:
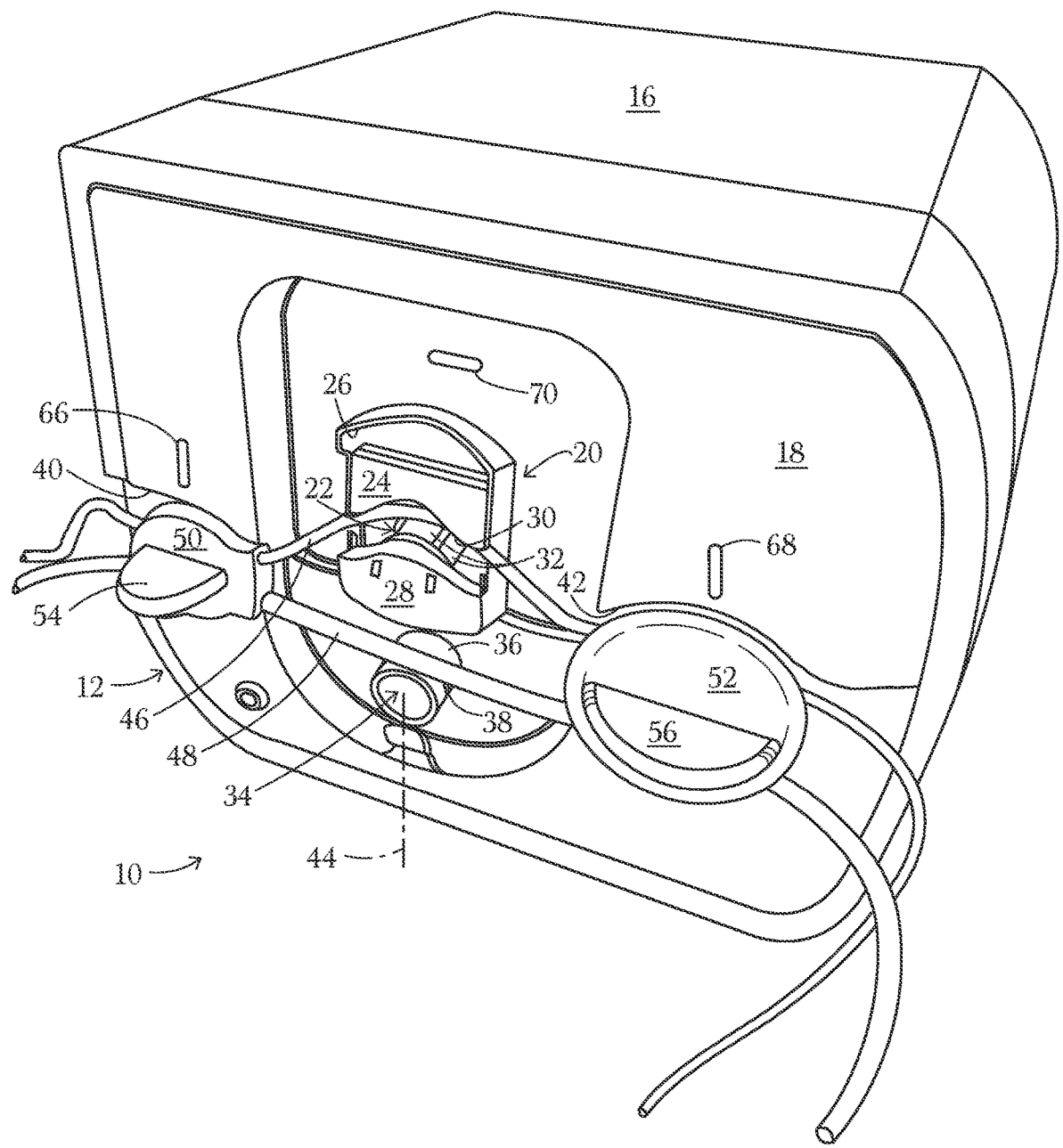
FIG. 2 is a perspective view of the system of FIG. 1, showing the tubing system positioned on the console, with an irrigation tube between an anvil and a roller set of a peristaltic pump.
Figure 3:
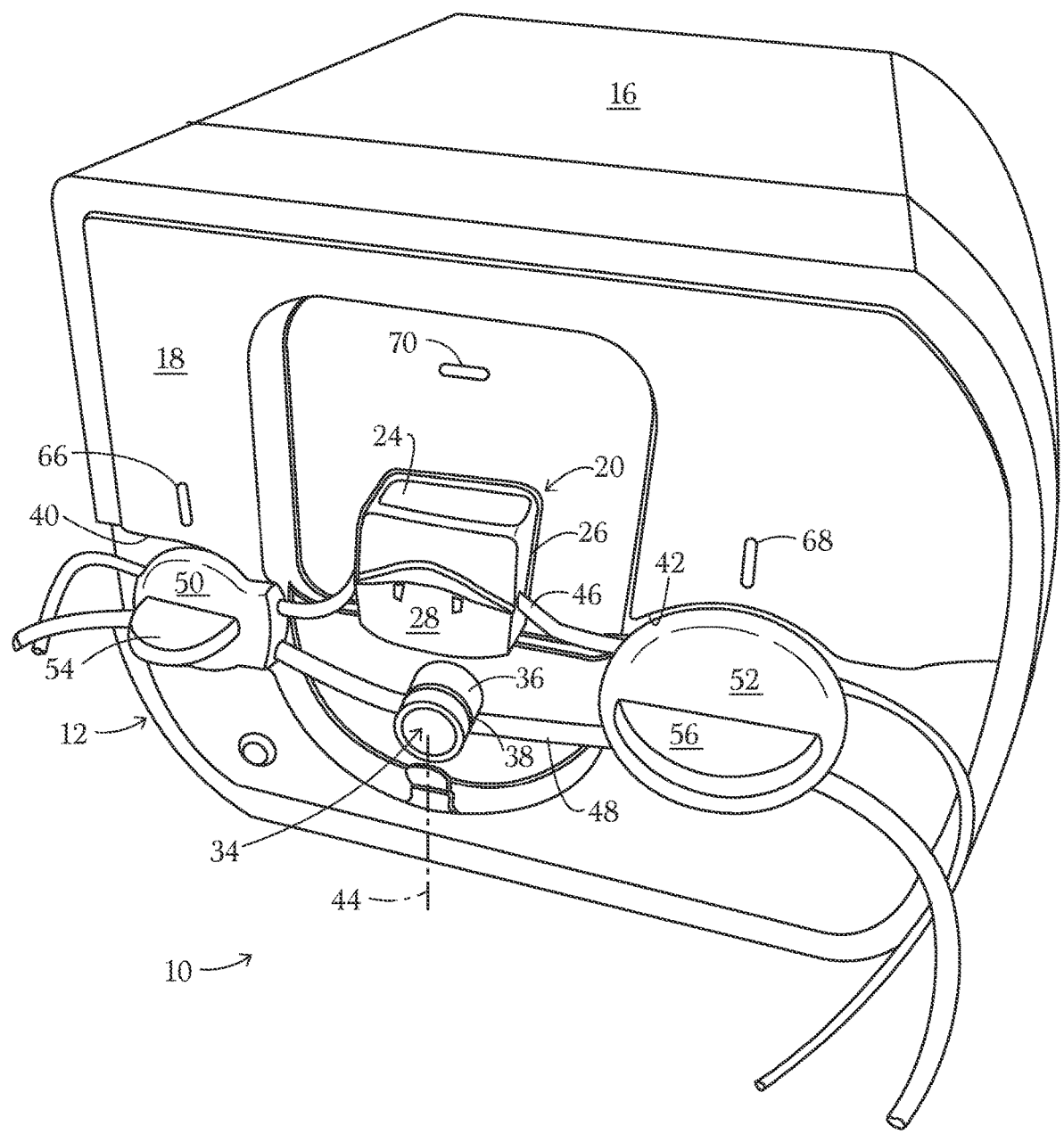
FIG. 3 is a perspective view similar to FIG. 2, showing a cover of the peristaltic pump closed over the irrigation tube and further showing an aspiration tube inserted between jaws (or an anvil and jaw) of a pinch solenoid on the console.

Disks 50 and 52 are spaced from one another by lengths of tubes 46 and 48 that are approximately equal (and slightly greater) to the distance between seats 40 and 42. Disks 50 and 52 are held and manipulated via flanges or finger grips 54 and 56, to engage housing side panel 18 in recesses or seats 40 and 42. Upon a disposition of disks 50 and 52 in seats 40 and 42, irrigation tube 46 is placed over roller set 22 in a gap between anvil 24 and bracket 28, as shown in FIG. 2. One then rotates the cover 26, which is pivotably mounted to housing 16 via anvil 24, thereby moving the anvil towards roller set 22 and clamping tube 46 between anvil surface 30 and the rollers 32, as illustrated in FIG. 3. As further shown in FIG. 3, aspiration tube 48 is inserted into slot 38 of pinch valve 34.

Console 12 exhibits indicators lights 66, 68, 70 that turn from one color, such as red or blue to another color such as green upon a successful seating of disks 50 and 52 in seats 40 and 42 and a successful or effective disposition of tube 46 between pump set 22 and surface 30 of anvil 24.

Console 12 may also include an air bubble detector 72 within seat 42. Bubble detector 72 preferably takes the form of an ultrasonic sensor with transmitter and receiver elements (not separately depicted) disposed in respective halves 74 and 76 of a slotted projection. During a seating of attachment or coupling disk 52 in recess or seat 42, the detector 72 is inserted into a hole 80 in the rear or inner side of attachment disk 52. Irrigation tube 46 extends across the hole 80 so as to automatically insert into a slot (not designated) defined between receiver halves 74 and 76 in the detector 72 upon the seating of attachment disk 52 in seat 42.

Panel 18 is preferably a side panel of housing 16, and peristaltic pump 20 and pinch valve 34 are preferably located vertically one above the other. However different configurations are possible. The essential feature is that the shapes and or sizes of disks 50 and 52, as well as seats 40 and 42, preclude an incorrect positioning of tubes 46 and 48. Upon the placements of disks 50 and 52 in recesses 40 and 42, it is not possible to position aspiration tube 48 on roller set 22 in the gap between anvil 24 and bracket or bearing plate 28. Only irrigation tube 46 is positionable there.

Prior to an ultrasonic surgical procedure, wherein liquid irrigant or coolant is furnished to an ultrasonic instrument via tube 46 and removed from the surgical site via tube 48, tubing set 14 is manipulated as described above so as to dispose a portion of tube 46 in operative engagement with roller set 22 and anvil 24, and a portion of tube 48 is inserted into slot or gap 38 of pinch valve 34.

Pursuant to the present invention, tubing set 14 includes irrigant tube 46 and suction or aspiration tube 48 connected in parallel to one another via a pair of spaced fasteners, that is, disks 50 and 52. Fasteners or attachment disks 50 and 52 include magnetic elements and have with planar projections 54 and 56 that serve as grips for grasping between the forefingers and thumbs by a technician. Disks 50 and 52 are juxtaposed to delineated positions (recesses or seats 40 and 42) on side panel 18 of console 16 where the disks are secured to the console in a quick-release mode of attachment, owing to magnetic attraction. Console panel 18 features well-known prior-art peristaltic pump 20 and a well-known pinch solenoid 34 that are spaced from one another. Disks 50 and 52 are attached to console 16 on opposite sides of an imaginary line 44 or plane extending defined by the locations of peristaltic pump 22 and pinch solenoid 34, preferably one located above the other. After the magnetic attachment, irrigation tube 46 is inserted over the rollers 32 of pump 20 and a cover- or lid-type anvil 24 is pivoted into place so that irrigation tube 46 is pressed between the pump rollers 32 and a curved inner surface 30 of the anvil. Aspiration tube 48 is placed in a gap 38 defined between jaws (not visible owing to sleeve 36) of pinch solenoid 34. Tubing set 14 simplifies the process of tube placement, making it impossible to insert the aspiration tube 48 into peristaltic pump 20.

Disk 50 or 52 may be provided with an RFID tag or chip (not shown) that may be set by a transmitter in housing 16 to prevent re-use of the tubing set 14, primarily for ensuring sterility.

Although the invention has been described in terms of particular embodiments and applications, one of ordinary skill in the art, in light of this teaching, can generate additional embodiments and modifications without departing from the spirit of or exceeding the scope of the claimed invention. Moreover, the phase shift might be varying, for instance, where the vibration modes are of different frequencies. Accordingly, it is to be understood that the drawings and descriptions herein are proffered by way of example to facilitate comprehension of the invention and should not be construed to limit the scope thereof.

What is claimed is:

1. A fluid handling tubing set for use in surgical interventions, said tubing set utilizable with a console including:
   a housing having a panel;
   a peristaltic pump mounted to said housing and extending outwardly from said panel, said pump including a roller set and an anvil movably attached to said panel;
   a pinch valve mounted to said housing, said pinch valve having a slot or gap between two jaws movable relative to one another, said peristaltic pump and said pinch valve being spaced along a line from one another; and
   a first seat and a second seat on said panel on opposite sides of said line,
   said tubing set including:
   an irrigation tube;
   an aspiration tube;
   a first disk having a first coupling element for attaching a major outer side or face of said first disk to said panel of said console; and
   a second disk having a second coupling element for attaching a major outer side or face of said second disk to said panel of said console, said irrigation tube and said aspiration tube each being coupled to both said first disk and said second disk so that said irrigation tube and said aspiration tube extend parallel to said panel and in spaced relation to one another between said first disk and said second disk and are respectively operatively engageable with said peristaltic pump and said pinch valve upon attachment of said first disk and said second disk to said panel at said first seat and said second seat respectively, said first disk being configured for attachment to said panel only in said first seat and said second disk being configured for attachment to said panel only in said second seat with said first disk and said second disk extending parallel to said panel.

2. The tubing set defined in claim 1 wherein said console includes coupling elements that cooperate with said first coupling elements and said second coupling element to releasably fasten said first disk and said second disk to said panel at said first seat and said second seat, respectively.

3. The tubing set defined in claim 2 wherein at least a plurality of said first coupling element, said second coupling element, and said coupling elements of said console include magnets.

4. The tubing set defined in claim 2 wherein said first disk and said second disk are disks of different sizes.

5. The tubing set defined in claim 1 wherein said first disk and said second disk have different geometries.

6. A method for use ancillary to a surgical procedure, comprising:
   providing a tubing set for carrying fluids, said tubing set including a first tube, a second tube, a first attachment element, and a second attachment element, said first tube and said second tube each being coupled to both said first attachment element and said second attachment element, said first attachment element and said second attachment element having different geometries;
   seating said first attachment element in a first seat on a panel of a console and said second attachment element in a second seat on said panel of said console so that said first tube and said second tube extend in spaced relation to one another between said first attachment element and said second attachment element;

thereafter manipulating said first tube so as to dispose a portion of said first tube in operative engagement with a roller set and an anvil of said console projecting from said panel; and also thereafter manipulating said second tube so as to insert said second tube into a slot or gap of a pinch valve of said console projecting from said panel.

7. A surgical console comprising:

a housing having a panel;

a peristaltic pump mounted to said housing and extending outwardly from said panel, said pump including a roller set and an anvil movably attached to said panel;

a pinch valve mounted to said housing, said pinch valve being different from said peristaltic pump and said roller set and anvil, said pinch valve having a slot or gap between two jaws movable relative to one another, said peristaltic pump and said pinch valve being spaced along a line from one another; and a first seat and a second seat on said panel on opposite sides of said line, said first seat and said second seat being differently configured to each receive only one of a pair of different attachment elements, a pair of tubes each being coupled to both said different attachment elements so that said tubes extend parallel to said panel and in spaced relation to one another between said different attachment elements and are operatively engageable with respective ones of said peristaltic pump and said pinch valve upon seating of said different attachment elements in predetermined ones of said first seat and said second seat.

8. The console defined in claim 7 wherein said seats have different geometries.

9. The console defined in claim 8 wherein said seats are recesses in said panel.

10. The console defined in claim 7, further comprising quick-release coupling elements mounted to said housing at said first seat and said second seat.

11. The console defined in claim 10 wherein said quick-release coupling elements are magnetic elements.

12. The console defined in claim 7, further comprising a plurality of indicators on said panel that signal successful placement of a first tube between said roller set and said anvil of said peristaltic pump and a second tube between said jaws.

13. The console defined in claim 12 wherein said indicators are lights.

14. The console defined in claim 7, further comprising an air bubble detector at said second seat, said air bubble detector being located to be juxtaposed to said irrigation tube upon seating of said second attachment element in said second seat.

15. The console defined in claim 14 wherein said air bubble detector is an ultrasound sensor.

16. The console defined in claim 7 wherein said panel is a side panel of said housing, said peristaltic pump and said pinch valve being located vertically one above the other.

* * * * *